(12) United States Patent
Derus et al.

(10) Patent No.: US 9,101,474 B2
(45) Date of Patent: Aug. 11, 2015

(54) IMPLANTABLE PENILE PROSTHESIS

(71) Applicant: AMS Research Corporation, Minnetonka, MN (US)

(72) Inventors: Patricia M. Derus, Rogers, MN (US); Carey J. Becker, Savage, MN (US); Gregory J. Henkel, Chanhassen, MN (US)

(73) Assignee: AMS Research Corporation, Minnetonka, MN (US)

( * ) Notice: Subject to any disclaimer, the term of this patent is extended or adjusted under 35 U.S.C. 154(b) by 184 days.

(21) Appl. No.: 13/863,713

(22) Filed: Apr. 16, 2013

(65) Prior Publication Data

US 2013/0324793 A1 Dec. 5, 2013

Related U.S. Application Data

(60) Provisional application No. 61/653,692, filed on May 31, 2012.

(51) Int. Cl.
 *A61F 5/00* (2006.01)
 *A61F 2/26* (2006.01)

(52) U.S. Cl.
 CPC ........................................ *A61F 2/26* (2013.01)

(58) Field of Classification Search
 CPC ........................................................ A61F 2/26
 USPC ................... 600/29–31, 38–41; 128/897–899
 See application file for complete search history.

(56) References Cited

U.S. PATENT DOCUMENTS

| | | | |
|---|---|---|---|
| 6,558,315 B1 | 5/2003 | Kuyava | |
| 6,935,847 B2 | 8/2005 | Kuyava et al. | |
| 7,066,877 B2 | 6/2006 | Kuyava | |
| 7,350,538 B2 | 4/2008 | Kuyava et al. | |
| 7,390,296 B2 | 6/2008 | Mische | |
| 7,438,682 B2 | 10/2008 | Henkel et al. | |
| 7,918,782 B2 | 4/2011 | George et al. | |
| 8,052,594 B2 | 11/2011 | George et al. | |
| 8,585,580 B2 * | 11/2013 | Vaingast et al. | ................ 600/37 |

OTHER PUBLICATIONS

AMS Solutions for Life™, "Information and Instructions for Patients Considering an AMS Ambicor® Penile Prosthesis," 2009 American Medical Systems, Inc. Order No. 23600005 (Jan. 2009).

* cited by examiner

*Primary Examiner* — John Lacyk
(74) *Attorney, Agent, or Firm* — Westman, Champlin & Koehler, P.A.

(57) ABSTRACT

A penile prosthesis includes an inflatable cylinder and a pump. The inflatable cylinder includes an inflatable volume extending within a front tip, a reservoir within a rear tip, and a deflation block. The deflation block is positioned between the inflatable volume and the reservoir, and includes a one-way valve configured to control a flow of fluid from the inflatable volume to the reservoir. The pump is configured to drive fluid from the reservoir and into the inflatable volume.

16 Claims, 3 Drawing Sheets

IMPLANTABLE PENILE PROSTHESIS

CROSS-REFERENCE TO RELATED APPLICATION

The present application is based on and claims the benefit of U.S. provisional patent application Ser. No. 61/653,692, filed May 31, 2012, the content of which is hereby incorporated by reference in its entirety.

FIELD

Embodiments of the invention are generally directed to implantable penile prostheses for treating erectile dysfunction. More specifically, embodiments are directed to a penile prosthesis having an improved inflation system for controlling inflation and deflation of the implantable penile prosthesis.

BACKGROUND

Erectile dysfunction is a psychological or physical disorder preventing males from forming or maintaining an erection during sexual intercourse. Erectile dysfunction is treatable through the implantation of a penile prosthesis. Typically, the penile prosthesis includes a pair of inflatable cylinders that are implanted in the corpus cavernosa of the penis and operate to mechanically erect the penis.

Each of the inflatable cylinders is operably linked to an inflation apparatus for selectively inflating the cylinder responsive to actuation of a pump. The inflation apparatus pumps an inflation fluid from a reservoir into the cylinder to inflate the cylinder and mimic an erection. The cylinder may be deflated by returning the fluid to the reservoir to transition the penile prosthesis to a flaccid state.

SUMMARY

Some embodiments of the invention are directed to a penile prosthesis and methods of operating the penile prosthesis. In some embodiments, the penile prosthesis includes an inflatable cylinder and a pump. The inflatable cylinder includes an inflatable volume extending within a front tip, a reservoir within a rear tip, and a deflation block. The deflation block is positioned between the inflatable volume and the reservoir, and includes a one-way valve configured to control a flow of fluid from the inflatable volume to the reservoir. The pump is configured to drive fluid from the reservoir and into the inflatable volume.

In other embodiments, the implantable penile prosthesis includes an inflatable cylinder, a fluid connector, a pair of one-way valves, and a pump. The inflatable cylinder includes an inflatable volume extending within a front tip, a reservoir within a rear tip, and a deflation block. The deflation block is positioned between the inflatable volume and the reservoir, and is configured to control a flow of fluid from the inflatable volume to the reservoir. The fluid connector extends from the cylinder and includes a first end and a second end. The second end is forked into an inflation branch, which is fluidically coupled to the inflation volume, and a reservoir branch, which is fluidically coupled to the reservoir. One of the one-way valves is in the reservoir branch and is configured to allow fluid travel through the reservoir branch and only in the inflation direction. The other one-way valve is in the inflation branch and is configured to allow fluid travel through the inflation branch in only the inflation direction. The pump is attached to the first end of the fluid connector and is configured to drive fluid from the reservoir in the inflation direction through the reservoir branch and the inflation branch, and into the inflatable volume.

Some embodiments of the invention are directed to a method of operating a penile prosthesis, which includes an inflatable cylinder having an inflatable volume extending within a front tip, a reservoir within a rear tip, and a deflation block position between the inflatable volume and the reservoir. In some embodiments of the method, a pump coupled to a first end of a fluid connector that extends from the inflatable cylinder is actuated. Fluid is driven from the reservoir through a reservoir branch and an inflation branch of a forked second end of the fluid connector, and into the inflatable volume responsive to actuating the pump. Internal pressure within the inflatable volume is increased to a threshold pressure. Fluid is driven from the inflatable volume to the reservoir through the deflation block responsive to increasing the internal pressure within the inflatable volume.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
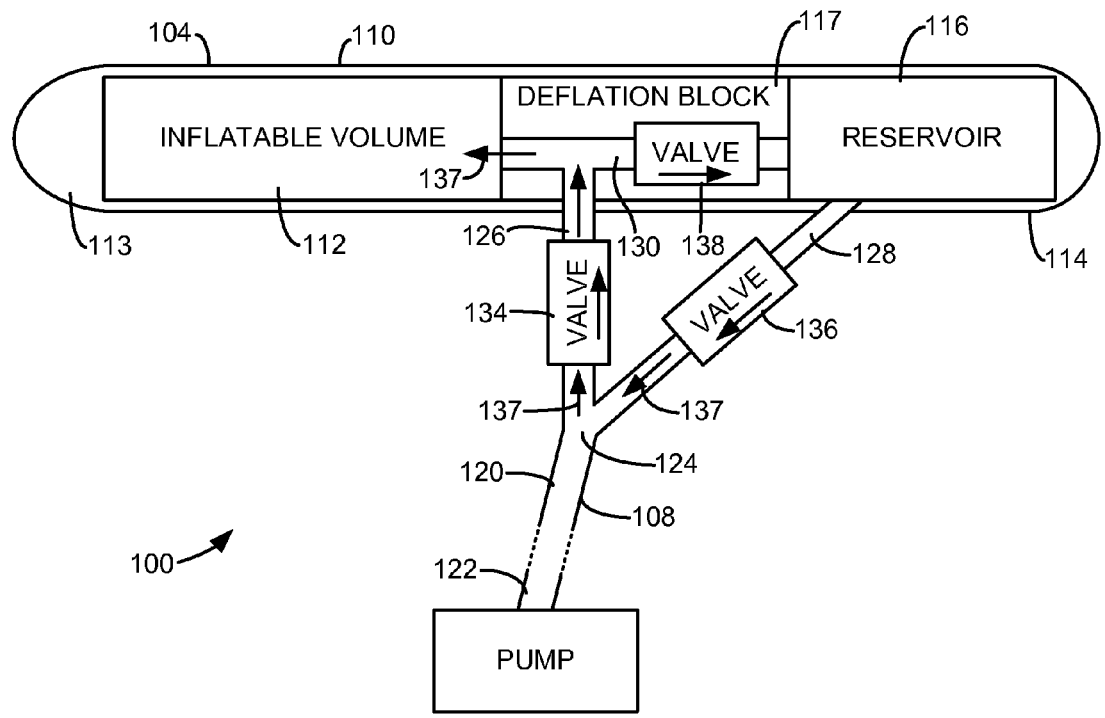
FIGS. 1 and 2 are simplified diagrams of an implantable penile prosthesis in accordance with embodiments of the invention illustrating inflation and deflation operations, respectively.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

Figure 2:
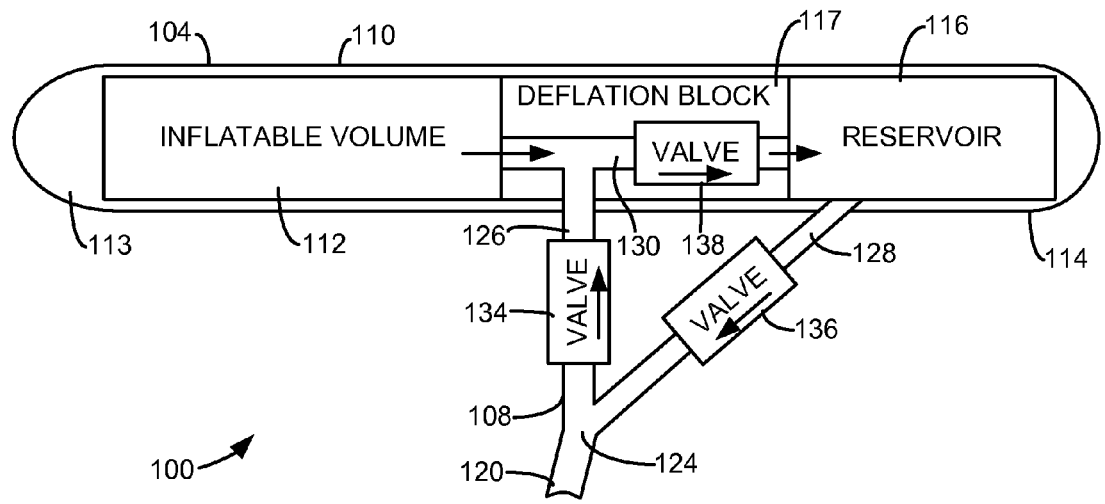
Figure 3:
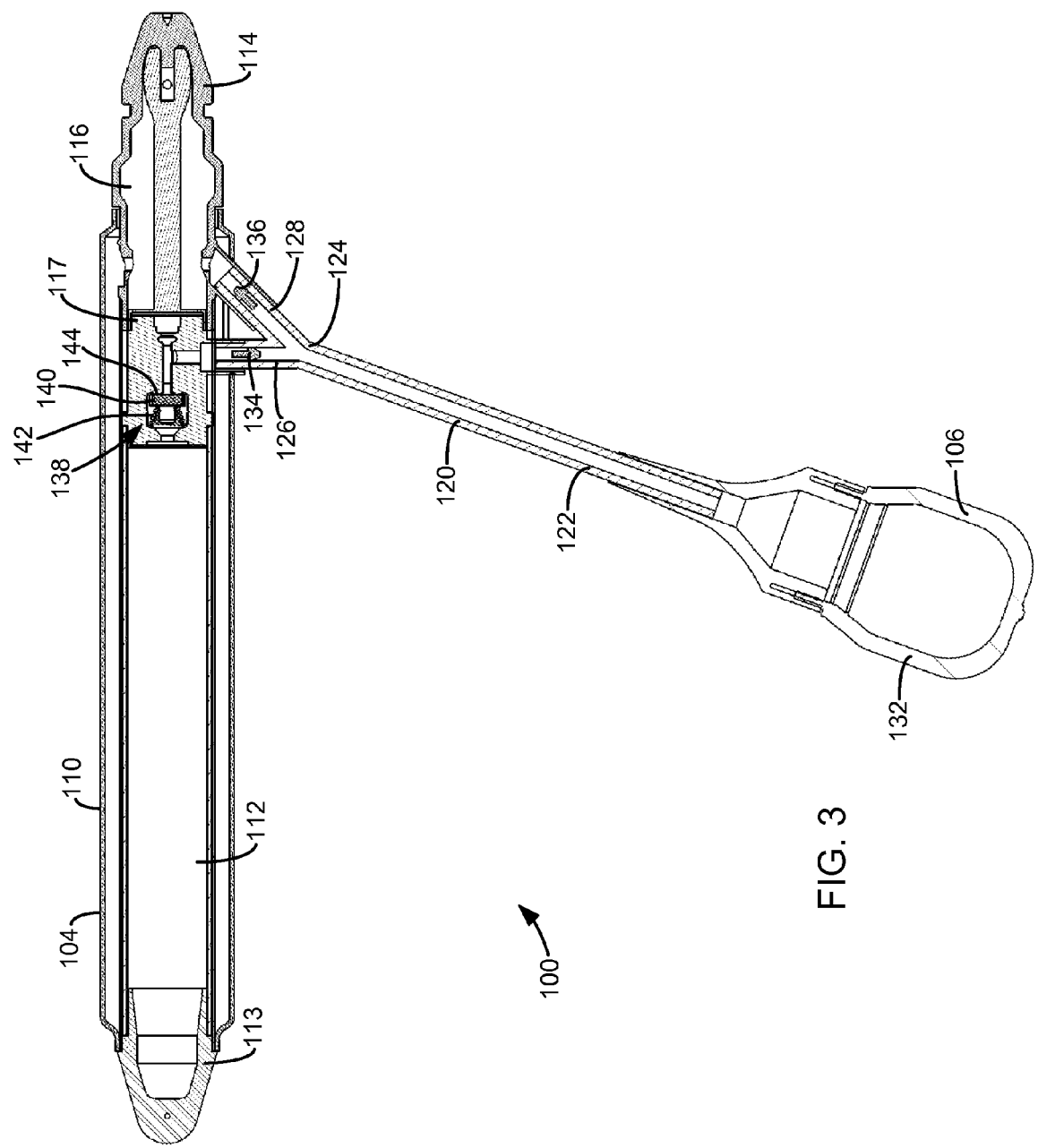
FIG. 3 is a cross-sectional view of an implantable penile prosthesis in accordance with embodiments of the invention.

FIGS. 1 and 2 are simplified diagrams of an implantable penile prosthesis 100 in accordance with embodiments of the invention respectively illustrating inflation and deflation operations. FIG. 3 is a cross-sectional view of an implantable penile prosthesis 100 in accordance with embodiments of the invention. In some embodiments, the penile prosthesis 100 includes at least one inflatable cylinder 104 that is each operably linked to a pump 106 via a fluid connector 108, which extends outside the cylinder 104. In some embodiments, the prosthesis 100 includes a pair of the cylinders 104 that are each operably linked to the pump 106 through separate fluid connectors 108. In order to simplify the drawings, only a single cylinder 104 and fluid connector 108 are illustrated.

In some embodiments, the inflatable cylinder 104 comprises an inflatable portion 110 defining an inflatable volume 112 that extends from a middle section of the cylinder 104 to within a front tip 113. The inflatable cylinder includes a rear tip 114 that includes a reservoir 116. The inflatable cylinder 104 further comprises a deflation block 117 disposed between the inflatable volume 112 and the reservoir 116.

In some embodiments, the fluid connector 108 comprises a primary line 120 having a first end 122 and a second end 124 that is forked into an inflation branch 126 and a reservoir branch 128, which extend to the cylinder 104. In some embodiments, the inflation branch 126 is fluidically coupled to the inflation volume 112, and the reservoir branch 128 is fluidically coupled to the reservoir 116. In some embodiments, the inflation branch 126 is fluidically coupled to the inflation volume 112 through a fluid passageway 130 through the deflation block 117, as shown in FIG. 1.

In some embodiments, the first end 122 of the fluid connector 108 is fluidically connected to an output of the pump 106. Embodiments of the pump 106 include conventional penile prosthesis pumps that may be actuated to drive fluid into the inflatable volume 112 through the inflation branch 126 to stiffen the cylinder 104 to an erect state. In some embodiments, the pump 106 includes a pump body 132 (FIG. 3) that may be actuated by compressing the fluid-inflated pump body 132. This drives fluid into the inflatable volume 112. The pump body 132 then automatically expands back to its inflated state, which pulls fluid from the reservoir 116 into the primary line 120 and the pump body 132. This actuation of the pump 106 may be repeated until the cylinder 104 reaches a desired stiffness.

In some embodiments, the inflation branch 126 includes a one-way valve 134, and the reservoir branch 128 includes a one-way valve 136. The valves 134 and 136, which are external to the cylinder 104, operate to allow fluid to flow from the reservoir 116 to the inflation volume 112 in an inflation direction (indicated by arrows 137) in response to actuation of the pump 106, as shown in FIG. 1. As the pump 106 is actuated by compressing the pump body 132, fluid in the line 120 is pressurized and driven through the valve 134 and into the inflation volume 112, as shown in FIG. 1. The valve 136 prevents the pressurized fluid from flowing to the reservoir 116 through the reservoir branch 128. As the pump body 132 re-inflates with fluid from the primary line 120, fluid is driven from the reservoir 116 through the valve 136 and into the primary line 120. Exemplary valves that may be used as the valves 134 and 136 include sleeve valves or other suitable one-way valves.

In some embodiments, the deflation block 117 includes a one-way valve 138 that is configured to control a flow of fluid from the inflatable volume 112 to the reservoir 116 to deflate the inflatable volume 112, as shown in FIG. 2. In some embodiments, the one-way valve 138 is maintained in a closed position during the inflation of the inflatable volume 112 in response to the actuation of the pump 106, as shown in FIG. 1. This prevents fluid from bleeding into the reservoir 112 under normal circumstances. In some embodiments, the one-way valve 138 transitions to an open position when the pressure of the fluid within the inflatable volume 112 reaches a predetermine threshold, allowing fluid to flow from the inflatable volume 112 to the reservoir 116, as shown in FIG. 1. The valve 134 prevents the fluid from flowing back through the fluid connector 108. In some embodiments, the inflatable cylinder 104 is adapted to be manually bent to increase the pressure of the fluid within the inflatable volume 112 to the threshold pressure and open the valve 138.

In some embodiments, the one-way valve 138 includes a poppet valve comprising a poppet 140 and a poppet spring 142. The poppet spring 142 biases the poppet 140 against a valve seat 144 to maintain the valve 138 in the closed position. When the pressure of the fluid within the inflatable volume 112 reaches or exceeds the threshold pressure by, for example, bending the inflatable cylinder 104, the bias force applied by the spring 142 is overcome, and the poppet 140 lifts off the valve seat 144. This opens the valve 138 and fluid flows through the valve 138 to the reservoir 116, as indicated in FIG. 2.

The exterior inflation valve system comprising one-way valves 134 and 136 frees up interior space of the cylinder 104 to allow the deflation block 117 to be positioned at the rear of the cylinder 104. This position of the deflation block 117 provides advantages over penile prostheses of the prior art that position a deflation block at the front tip of the inflation cylinder, which leads to patient discomfort. By positioning the deflation block 117 rearward of the front tip 113 between the inflatable volume 112 and the reservoir 116, this discomfort is eliminated without sacrificing the easy deflation method of simply bending the inflatable portion of the cylinder 104.

Figure 4:
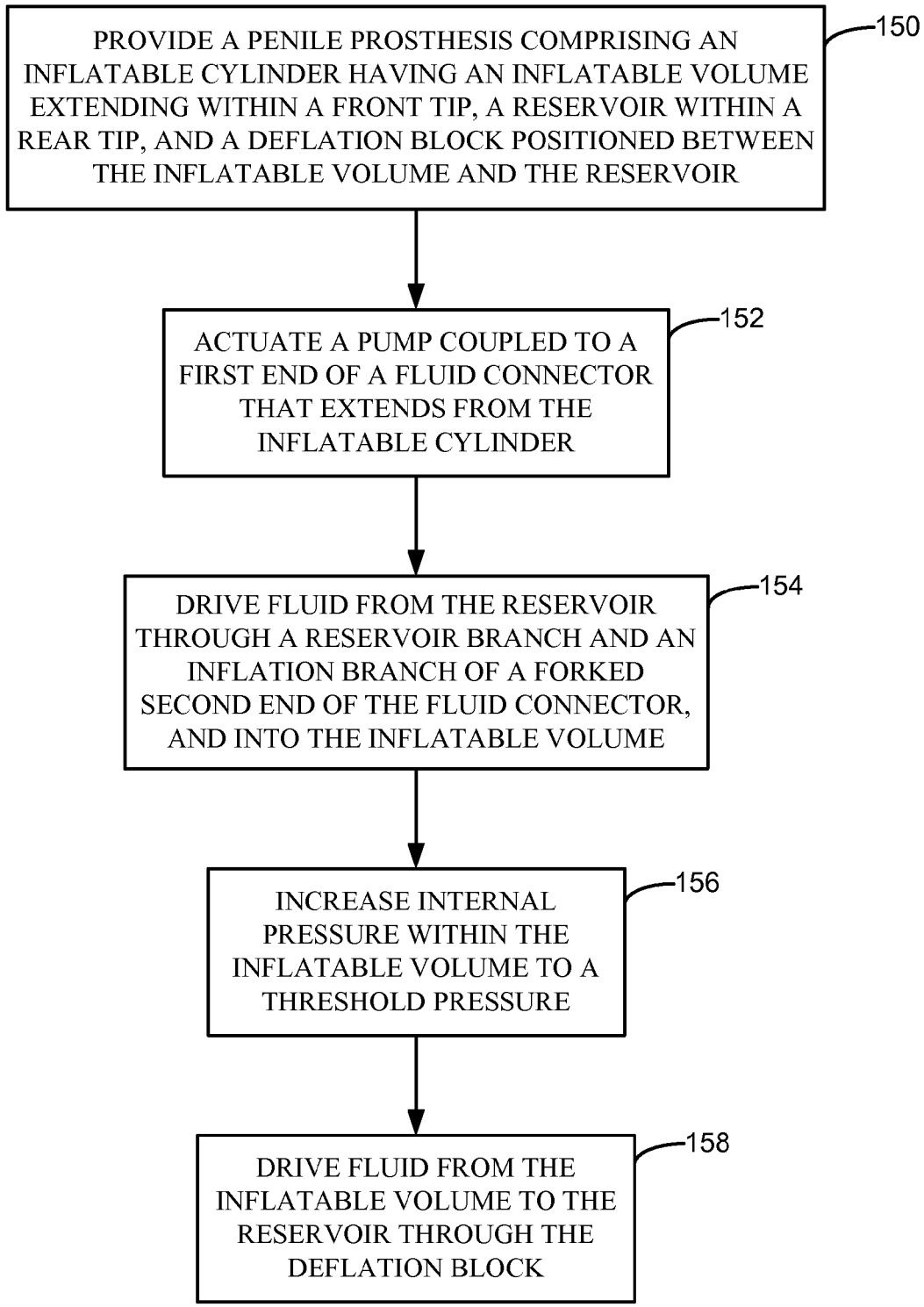
FIG. 4 is a flowchart illustrating a method of operating a penile prosthesis in accordance with embodiments of the invention.

FIG. 4 is a flowchart illustrating embodiments of a method of operating a penile prosthesis 100 formed in accordance with one or more embodiments described above. In some embodiments, a penile prosthesis 100 is provided at step 150. In some embodiments, the penile prosthesis includes an inflatable cylinder 104 having an inflatable volume 112 extending within a front tip 113, a reservoir 116 within a rear tip 114, and a deflation block 117 positioned between the inflatable volume 112 and the reservoir 116, as shown in FIGS. 1 and 3. At 152 of the method, a pump 106 coupled to a first end 122 of a fluid connector 108 that extends from the cylinder 104 is actuated. This may involve squeezing or compressing a pump body 132 (FIG. 3), as discussed above. At 154, fluid is driven from the reservoir 116 through a reservoir branch 128 and an inflation branch 126 of a forked second end 124 of the fluid connector 108, and into the inflatable volume 112. This stiffens the cylinder 104 to place it in an erect state.

At 156, internal pressure within the inflatable volume 112 is increased to a threshold pressure. This may occur by squeezing or bending the cylinder 104, as discussed above. Fluid is driven from the inflatable volume 112 to the reservoir 116 through the deflation block 117, at 158, in response to step 156. This deflates the cylinder 104 and places it in a flaccid state.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative embodiments.

What is claimed is:

1. An implantable penile prosthesis comprising:
    an inflatable cylinder comprising:
        an inflatable volume extending within a front tip;
        a reservoir within a rear tip; and
        a deflation block positioned between the inflatable volume and the reservoir and including a one-way valve configured to control a flow of fluid from the inflatable volume to the reservoir; and
    a pump configured to drive fluid from the reservoir and into the inflatable volume.

2. The penile prosthesis of claim 1, wherein:
    the penile prosthesis comprises a fluid connector extending from the cylinder and including a first end and a second end, wherein the second end is forked into an inflation branch, which is fluidically coupled to the inflation volume, and a reservoir branch, which is fluidically coupled to the reservoir; and the pump is attached to the first end of the fluid connector and is configured to drive fluid from the reservoir in an inflation direction through the reservoir branch and the inflation branch, and into the inflatable volume.

3. The penile prosthesis of claim 2, wherein the inflation branch is fluidically coupled to the inflatable volume via a fluid passageway through the deflation block.

4. The penile prosthesis of claim 2, further comprising a one-way valve in the reservoir branch configured to allow fluid travel through the reservoir branch in only the inflation direction.

5. The penile prosthesis of claim 4, further comprising a one-way valve in the inflation branch configured to allow fluid travel through the inflation branch in only the inflation direction.

6. The penile prosthesis of claim 1, wherein the one-way valve of the deflation block comprises a poppet valve comprising a poppet and a poppet spring, the poppet spring biases the poppet in a closed position, in which fluid flow from the inflatable volume to the reservoir is prevented.

7. The penile prosthesis of claim 6, wherein:
the poppet is driven to an open position responsive to a pressure within the inflatable volume exceeding a threshold pressure; and
fluid travels from the inflatable volume through the poppet valve and into the reservoir when the poppet is in the open position.

8. An implantable penile prosthesis comprising:
an inflatable cylinder comprising:
an inflatable volume extending within a front tip;
a reservoir within a rear tip; and
a deflation block positioned between the inflatable volume and the reservoir configured to control a flow of fluid from the inflatable volume to the reservoir;
a fluid connector extending from the cylinder and including a first end and a second end, wherein the second end is forked into an inflation branch, which is fluidically coupled to the inflation volume, and a reservoir branch, which is fluidically coupled to the reservoir;
a one-way valve in the reservoir branch configured to allow fluid travel through the reservoir branch in only an inflation direction;
a one-way valve in the inflation branch configured to allow fluid travel through the inflation branch in only the inflation direction; and
a pump attached to the first end of the fluid connector and configured to drive fluid from the reservoir in the inflation direction through the reservoir branch and the inflation branch, and into the inflatable volume.

9. The penile prosthesis of claim 8, wherein the deflation block includes a one-way valve configured to control a flow of fluid from the inflatable volume to the reservoir.

10. The penile prosthesis of claim 9, wherein the one-way valve of the deflation block comprises a poppet valve comprising a poppet and a poppet spring, the poppet spring biases the poppet in a closed position, in which fluid flow from the inflatable volume to the reservoir is prevented.

11. The penile prosthesis of claim 10, wherein:
the poppet is driven to an open position responsive to a pressure within the inflatable volume exceeding a threshold pressure; and
fluid travels from the inflatable volume through the poppet valve and into the reservoir when the poppet is in the open position.

12. The penile prosthesis of claim 9, wherein the inflation branch is fluidically coupled to the inflatable volume via a fluid passageway through the deflation block.

13. A method of operating a penile prosthesis, which includes an inflatable cylinder having an inflatable volume extending within a front tip, a reservoir within a rear tip, and a deflation block positioned between the inflatable volume and the reservoir, the method comprising:
actuating a pump coupled to a first end of a fluid connector that extends from the inflatable cylinder;
driving fluid from the reservoir through a reservoir branch and an inflation branch of a forked second end of the fluid connector, and into the inflatable volume responsive to actuating a pump;
increasing internal pressure within the inflatable volume to a threshold pressure; and
driving fluid from the inflatable volume to the reservoir through the deflation block responsive to increasing internal pressure within the inflatable volume.

14. The method of claim of claim 13, wherein driving fluid from the reservoir comprises driving fluid in an inflation direction through a one-way valve in the reservoir branch and a one-way valve in the inflation branch.

15. The method of claim 14, wherein driving fluid from the inflatable volume to the reservoir comprises driving fluid through a one-way valve of the deflation block.

16. The method of claim 15, wherein driving fluid through a one-way valve of the deflation block comprises transitioning the one-way valve from a closed position to an open position responsive to increasing internal pressure within the inflatable volume.

* * * * *

UNITED STATES PATENT AND TRADEMARK OFFICE
CERTIFICATE OF CORRECTION

| | | |
|---|---|---|
| PATENT NO. | : 9,101,474 B2 | Page 1 of 1 |
| APPLICATION NO. | : 13/863713 | |
| DATED | : August 11, 2015 | |
| INVENTOR(S) | : Derus et al. | |

It is certified that error appears in the above-identified patent and that said Letters Patent is hereby corrected as shown below:

IN THE SPECIFICATION:

In Column 3, Lines 54-55, delete "reservoir 112" and insert -- reservoir 116 --, therefor.

IN THE CLAIMS:

In Column 6, Line 38, in Claim 14, delete "of claim of claim" and insert -- of claim --, therefor.

Signed and Sealed this
Ninth Day of February, 2016

Michelle K. Lee
*Director of the United States Patent and Trademark Office*